United States Patent [19]

Toepfl

[11] 4,004,914
[45] Jan. 25, 1977

[54] THIOLCARBAMATES FOR COMBATING UNDESIRED PLANT GROWTH

[75] Inventor: Werner Toepfl, Basel, Switzerland

[73] Assignee: Ciba-Geigy AG, Basel, Switzerland

[22] Filed: Aug. 4, 1975

[21] Appl. No.: 601,962

Related U.S. Application Data

[62] Division of Ser. No. 84,465, Oct. 27, 1970, abandoned.

[30] Foreign Application Priority Data

Nov. 3, 1969 Switzerland .................... 16351/69

[52] U.S. Cl. .............................. 71/100; 260/455 A
[51] Int. Cl.$^2$ ......................................... A01N 9/12
[58] Field of Search .................. 71/100; 260/455 A

[56] References Cited

UNITED STATES PATENTS

| 3,298,817 | 1/1967 | Tilles et al. ..................... 260/455 A |
| 3,582,314 | 6/1971 | Konnai et al. ........................ 71/100 |
| 3,682,616 | 8/1972 | Kimura et al. ........................ 71/100 |
| 3,822,124 | 7/1974 | Konnai et al. ........................ 71/100 |

FOREIGN PATENTS OR APPLICATIONS 886,425   1/1962   United Kingdom ................. 71/100

*Primary Examiner*—Glennon H. Hollrah
*Attorney, Agent, or Firm*—Frederick H. Rabin

[57] ABSTRACT

N-alkyl-N-alkenyl-S-benzyl-thiolcarbamates have been found to be very effective weed killers. They may be used without a carrier or in the form of herbicidal compositions preferably for combating grasslike weeds in rice cultures.

3 Claims, No Drawings

THIOLCARBAMATES FOR COMBATING UNDESIRED PLANT GROWTH

This is a division of application Ser. No. 84,465 filed on Oct. 27, 1970, now abandoned.

The present invention relates to new thiolcarbamates, their manufacture and use in combating undesired plant growth. The invention also relates to compositions that contain these compounds as active substances.

The new compounds correspond to the general formula

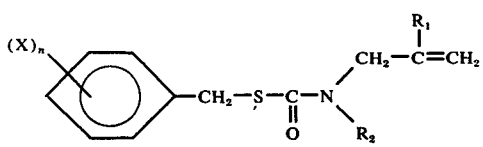

wherein X denotes a halogen atom, $n$ is an integer representing the number 0 or 1, $R_1$ denotes a hydrogen or chlorine atom or a methyl group, and $R_2$ represents a methyl, ethyl, n-propyl or isopropyl group.

Preferred are compounds in which X is in 4-position and, among them compounds in which X denotes a chlorine atom.

Undesirable grasses, such as Echinochloa (for example, Echinochloa crusgalli) in rice cultures can be combated selectively by the thiolcarbamates of formula I. It is quite immaterial here whether the active substances be applied before or after the rice plants have sprouted; the culture will not be harmfully affected in any way. The compounds according to the invention possess a surprising advantage over the known grass herbicide for rice cultures, N-N-diethyl-S-(p-chlorobenzyl)-thiolcarbamate, which causes considerable damage to the rice cultures in the pre-emergence treatment.

The compounds of formula I can also be used, however, for combating undesired plant growth in other crop plant cultures, such as grain crops in the widest sense of the term, for example, rye, oats, wheat barley, rice and corn or sugar beet, soya, potatoes, etc.

The compounds display a very good activity in the pre-emergent and post-emergent treatment if an amount of active substance in the range of 0.5 to 5 kg per hectare is applied.

The thiolcarbamates of formula I possess, moreover, in the appropriate rates of application the property of exerting a favorable influence on food plants. They may be used, for example, in thinning out fruit before harvesting, for controlling grass growth, or for internodial shortening in growing grain in order to increase its stability.

The compounds of formula I may also be used for accelerating the growth in plants by premature drying; further, for increasing the fruit setting, delaying the blossoming, extending the storage life of crops or for rendering plants resistant to frost. The use of these active substances as growth inhibitors may increase the crop yield not only by suppressing weed growth, but also by the fact that these active substances combat factors that stimulate the growth of the cultivated plants in an undesired manner, for example, high temperature or over-fertilization. On the other hand, the compounds of formula I may be used with advantage as herbicides for exterminating tenacious weeds in the long term, if instant application does not achieve satisfactory results.

The compounds of formula I may be applied by themselves or together with a suitable carrier and/or other additives. Suitable carriers and additives may be solid or liquid and correspond to the substances conventionally used in formulation technique, for example, natural or regenerated mineral substances, solvents, diluents, dispersants, wetting agents adhesives, thickeners, binders or fertilizers. It is also possible to add further plant-influencing compounds which may belong, for example, to the group of the phenoxyalkylcarboxylic acids (2,4-D-type) and achieve with the compounds of formula I a synergistic effect. They may, however, also belong to the class of the ureas, the saturated or unsaturated halogenated fatty acids, halobenzonitriles, halobenzoic acids, carbamates, triazines, nitroalkylphenols, organic phosphoric compounds, quaternary ammonium salts, sulphamic acids, arsenates, arsenites, borates or chlorates. The herbicidal preparations may be manufactured, for example, from a combination of the following ingredients:

A. Substituted ureas

N-Phenyl-N',N'-dimethylurea, N-phenyl-N-hydroxy-N',N'-dimethylurea, N-(4-chlorophenyl)-N',N'-dimethylurea, N-(3,4)-dichlorophenyl)-N',N'-dimethylurea, N-(3,4-dichlorophenyl)-N-benzoyl-N',N'-dimethylurea, N-(4-chlorophenyl)-N'-methoxy-N'-methylurea, N-(4-chlorophenyl)-N'-isobutinyl-N'-methylurea, N-(3,4-dichlorophenyl)-N'-methoxy-N'-methylurea, N-(4-bromophenyl)-N-'-methoxy-N'-methylurea, N-(4-chlorophenyl)-N'-methyl-N'-butylurea, N-(4-chlorophenyl)-N'-methyl-N'-isobutylurea, N-(2-chlorophenoxyphenyl)-N',N'-dimethylurea, N-(4-chlorophenoxyphenyl)-N',N'-dimethylurea, N-(4-chlorophenyl)-N'-methyl-N'-(1-butin-2-yl)urea, N-benzthiazol-2-yl-N',N'-dimethylurea, N-benzthiazol-2-yl-N'-methylurea, N-(3-trifluoromethyl-4-methoxyphenyl)-N',N'-dimethylurea, N-(3-trifluoromethyl-4-isopropoxyphenyl)-N',N'-dimethylurea, N-(3-trifluoromethylphenyl)-N',N'-dimethylurea, N-(4-trifluoromethylphenyl)-N',N'-dimethylurea, N-(4-chlorophenyl)-N'-(3'-trifluoromethyl-4'-chlorophenyl)urea, N-(3,4-dichlorophenyl)-N'-methyl-N'-butylurea, N-(3-chloro-4-trifluoromethylphenyl)-N',N'-dimethylurea, N-(3-chloroethylphenyl)-N',N'-dimethylurea, N-(3-chloro-4-methylphenyl)-N',N'-dimethylurea, N-(3-chloroethoxyphenyl)-N'-methyl-N'-methoxyurea, N-(3-chloro-4-methoxyphenyl)-N',N'-dimethylurea, N-(hexahydro-4,7-methanoindan-5-yl)-N',N'-dimethylurea, N-(2-methylcyclohexyl)-N'-phenylurea, N-(4,6-dichloro-2-pyridyl)-N'-dimethylurea, N'-cyclooctyl-N,N-dimethylurea, dichlorourea, N'-4-(4-methoxyphenoxy)phenyl-N,N-dimethylurea, N'-(3-methylphenyl)-N,N-dimethylthiourea, 1,1-dimethyl-3-[3-(N-tert.butylcarbamoyloxy)-phenyl]-urea, O,N,N-trimethyl-N'-4-chlorophenylisourea, N-3,4-dichlorophenyl-N',N'-dimethyl-α-chloroformamidine, N,N-dimethyl-N'-phenylurea trichloroacetate, N,N-dimethyl-N'-4-chlorophenylurea trichloroacetate.

B. Substituted triazines

2-Chloro-4,6-bis(ethylamino)-s-triazine, 2-chloro-4-ethylamino-6-isopropylamino-s-triazine, 2-chloro-4,6-bis(methoxypropylamino)-s-triazine, 2-methoxy-4,6-bis(isopropylamino)-s-triazine, 6-diethylamino-4-isopropylacetamido-6-methoxy-s-triazine, 2-isopropylamino-4-methoxyethylamino-4-methylmercapto-s-triazine, 2-methylmercapto-4,6-bis(isopropylamino)-s-triazine, 2-methylmercapto-4,6-bis(ethylamino)-s-triazine, 2-methylmercapto-4-ethylamino-6-tert.butylamino-s-triazine, 2-methylmercapto-4-ethylamino-6-isopropylamino-s-triazine, 2-methylmercapto-4-methylamino-6-isopropylamino-s-triazine, 2-methoxy-4,6,4,6-bis(ethylamino)-s-triazine, 2-methoxy-4-ethylamino-6-isopropylamino-s-triazine, 2-chloro-4,6-bis-(isopropylamino)-s-triazine, 2-azido-4-methylmercapto-6-isopropylamino-s-triazne, 2-azido-4-methylmercapto-6-sec,butylamino-s-triazine, 2-chloro-4-isopropylamino-6-(γ-methoxypropylamino)-s-triazine, 2-(6-ethylamino-4-chloro-s-triazin-2-ylamino)-2-methylpropionitrile, 2-chloro-4-diethylamino-6-isopropylamino-s-triazine, 2-methoxy-4,6-bis(3-methoxypropylamino)-s-triazine, 2-methylmercapto-4-isopropylamino-6-(3-methoxypropylamino)-s-triazine, 2-chloro-4-diethylamino-6-ethylamino-s-triazine, 2,4-bis(3-methoxypropylamino-6-methylthio)-1,3,5-triazine, 2-methylthio-4-isopropylamino-6-(γ-methoxypropylamino)-1,3,5-triazine, 2-chloro-4-ethylamino-6-tert.butylamino-s-triazine, 2-(4-chloro-6-ethylamino-1,3,5-triazin-2yl-amino)-2-methylpropionitrile.

C. Phenols

Dinitro-sec.butylphenol or salts thereof, pentachlorophenol or salts thereof, 3,5-dinitro-ortho-cresol, 2,6-dibromo-4-cyanophenol, 2,6-dichloro-4-cyanophenol salts or esters, dinitro-tert.butylphenol salts or esters, dinitro-sec.amylphenol salts or esters, 2-ethoxymethyl-4,6-dinitrophenol salts or esters, 2-tert.butyl-4,6-dinitro-5-methylphenol salts or esters.

D. Carboxylic acids, their salts or esters 2,4,6-Trichlorophenylacetic acid, 2,3,6-trichlorobenzoic acid or salts thereof, 2,3,5,6-tetrachlorobenzoic acid or salts thereof, 2,3,5,6-tetrachloroterephthalic acid, 2-methoxy-3,5,6-trichlorobenzoic acid or salts thereof cyclopropanecarboxylic acid-2,4-dinitro-6-sec.butylphenyl ester, cyclopentanecarboxylic acid-2,4-dinitro-6-sec.butylphenyl ester, 2-methoxy-3,6-dichlorobenzoic acid or salts thereof, 2-amino-2,5-dichlorobenzoic acid or salts thereof, 3-nitro-2,5-dichlorobenzoic acid or salts thereof, 2-methyl-3,6-dichlorobenzoic acid or salts thereof, 2,4-dichlorophenoxyacetic acid salts or esters, 2,4,5-trichlorophenoxyacetic acid salts or esters, (2-methyl-4-chlorophenoxy)acetic acid salts or esters, 2-(2,4,5-trichlorophenoxy)propionic acid salts or esters, 2-(2,4,5-trichlorophenoxy)ethyl-2,2-dichloropropionic acid salts or esters, 4-(2,4-dichlorophenoxy)butyric acid salts or esters, 4-(2-methyl-4-chlorophenoxy)butyric acid salts or esters methyl-2-chloro-3-(4'-chlorophenyl)-propionate, 2-chloro-9-hydroxy-fluorene-9carboxylic acid, endo-oxo-hexahydrophthalic acid, tetrachlorophthalic acid dimethyl ester, 4-chloro-2-oxobenzothiazolin-3yl-acetic acid, 2,2,3-trichloropropionic acid salts or esters, 2,2-dichloropropionic acid salts or esters, (±)2-(2,4-dichlorophenoxy)-propionic acid salts or esters, 7-oxabicyclo(2.2.1)heptano-2,3-dicarboxylic acid, 4-chlorophenoxyacetic acid salts or esters, gibberellinic acid, indolylacetic acid, indolylbutyric acid, (±)2-(4-chloro-2-methylphenoxy)propionic acid salts or esters, N,N-diallylchloroacetamide, naphthylacetic acid, N-1-naphthyl-phthalimidic acid salts or esters, 4-amino-3,5,6-trichloropicolinic acid salts or esters, trichloroacetic acid, 4-(2,4,5-trichlorophenoxy)butyric acid salts or esters, 2,3,5-triiodobenzoic acid salts or esters, benzimidoxyacetic acid salts or esters, ethyleneglycol-bis-trichloroacetate, chloroacetic acid diethylamide, 2,6-dichlorothiobenzamide, 2,6-dichlorobenzonitrile, N,N-dimethyl-α,α-diphenylacetamide, diphenylacetonitrile, N-hydroxymethyl-2,6-dichlorothiobenzamide.

E. Carbamic acid derivatives

Carbanilic acid isopropyl ester, 3,4-dichlorocarbanilic acid methyl ester, meta-chlorocarbanilic acid isopropyl ester, meta-chlorocarbanilic acid-4-chloro-2-butinyl ester, meta-trifluoromethylcarbanilic acid isopropyl ester, 2,6-di-tert.-butyl-4-tolyl-N-methylcarbamate, 3-(methoxycarbonylamino)phenyl-N-3-tolylcarbamate, 4-chloro-2-butinyl-N-(3-chlorophenyl)-carbamate, methyl-2-isopropyl-4-(methylcarbamoyloxy)carbanilate, furthermore diallate, N,N-dipropyl-S-ethylthiocarbamate, molinates and dithiocarbamates of the formula

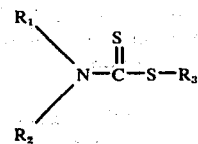

(in which $R_1$, $R_2$ and $R_3$ each represents a lower alkyl or alkenyl residue, or $R_1$ and $R_2$ together with the nitrogen atom linked with them form a possibly alkylated ring comprising 5, 6 or 7 members, which contains a total of 6 or 7 carbon atoms, in which the exo-alkyl groups must be linked with the carbon atoms vicinal to the nitrogen atoms, and $R_3$ represents an ethyl or a propyl, n-butyl or isobutyl residue, and among them especially:)

N-butyl-N-ethyl-S-propyl-dithiocarbamate, N,N-diisobutyl-S-propyl-dithiocarbamate, N,N,S-tripropyl dithiocarbamate, N-isobutyl-N-allyl-S-propyl dithiocarbamate, N-isobutyl-N-methallyl-S-ethyl dithiocarbamate, N-isobutyl-N-methallyl-S-propyl dithiocarbamate, N,N-dimethallyl-S-propyl dithiocarbamate, N-butyl-N-ethyl-S-propyl thiocarbamate and, N,N,S-tripropyl thiocarbamate, as well as N-(4-aminobenzosulphonyl)methyl carbamate, 1-methylprop-2-yl-N-(3-chlorophenyl)carbamate, isopropyl-N-(3chlorophenyl)carbamate, S-2,3-dichloroallyl-N,N-diisopropyl thiocarbamate, S-ethyl-N,N-dipropyl thiocarbamate, N-methyl-dithiocarbamic acid, S-propyl-N-butyl-N-ethyl thiocarbamate, 3-(meta-tolylcarbamoyloxy)-phenyl carbamate, isopropyl-N-phenyl carbamate, 2-chloroallyl-N,N-diethyl dithiocarbamate, methyl-N-(3,4-dichlorophenyl) carbamate, S-2,3,3-trichloroallyl-N,N-diisopropyl thiocarbamate, S-propyl-N,N-dipropyl thiocarbamate, S-ethyl-N-ethyl-thiocyclohexane carbamate, 3,4-dichlorobenzylmethyl carbamate, S-ethyl-N-hexahydrol-1H-azepine thiocarbamate, 2,6-di-tert.butyl-4-methylphenyl-N-methylcarbamate, methyl-N-(4-nitrobenzosulphonyl)carbamate, N,N-hexamethylene-S-isopropyl thiocarbamate, S-ethyl-N,N-diisobutyl thiocarbamate, 2-chlorobutinyl-N-(3-chlorophenyl) carbamate, S-ethyl-N,N-diisobutyl thiocarbamate, methyl-N'-(N'-methoxycarbamoyl-sulphanilyl) carbamate.

F. Anilides 3,4-Dichloropropionanilide, 3-chloro-4-bromopropionanilide, 3-bromo-4-chloropropionanilide, cyclopropanecarboxylic acid-3,4-dichloroanilide, cyclopropanecarboxylic acid-3-chloro-4-bromoanilide, cyclopropanecarboxylic acid-3-bromo-4-chloroanilide, N-(3,4-dichlorophenyl)-2-methylpentane amide, N-1-naphthyl-phthalamic acid, N-(3-tolyl)-phthalamic acid, 2-methacryl-3',4'-dichloroanilide, N-(4-chlorophenyl)-2,2-dimethyl valeramide, N-(3-chloro-4-methylphenyl)-2-methylpentane amide, α-chloro-N-isopropyl acetanilide 2-(α-naphthoxy)-N,N-diethyl propionamide, 2-chloro-N-(2-methyl-6-tert.butylphenyl)acetamide, 2-chloro-N-2,6-diethylphenyl-N-methoxymethylacetamide, 6-methyl-N-methoxymethyl-2-tert.butyl-α-bromoacetanilide, 2-[(4-chloro-ortho-tolyl)oxy]-N-methoxyacetamide, 2-chloro-N-isopropylacetanilide.

G. Organic phosphorus compounds tris-(2,4-Dichlorophenoxyethyl)phosphite, O-(2,4-dichlorophenyl)-O'-methyl-N-isopropyl-amido thiophosphate, N-[2-O,O-diisopropyl-dithiophosphoryl)ethyl]-benzenesulphonamide, S,S,S-tributyl thiophosphate.

H. Sundry compounds 4,5-Dichloro-2-trifluoromethyl benzimidazole, 2-chloroethyl-trimethyl-ammonium chloride, maleic acid hydrazide, methylarsinic acid di-sodium salt, 4,5,7-trichlorobenzthiodiazole-2,1,3, 3-amino-1,2,4-triazole, trichlorobenzylchloride, 2-phenyl-3,1-benzoxazinone, N-butyl-N-ethyl-2,6-dinitro-4-trifluoromethyl aniline, N,N-di-(n-propyl)-2,6-dinitro-4-trifluoromethyl aniline, 4-trifluoromethyl-2,4'-dinitro diphenyl ether, 2,4,6-trichloro-4'-nitrodiphenyl ether, 4-trifluoromethyl-2,4'-dinitro-3'-methyl diphenyl ether, 2,4-dichloro-4'-nitro diphenyl ether, 5-chloro-6-methyl-3-tert.butyluracil, ammonium sulphamate, 5-bromo-6-methyl-3-(1-methyl-N-propyl)-uracil 1,2,4,5,6,7,10,10-octachloro-4,7,8,9-tetrahydro-4,7-methyleneindane-meta-isopropyl xanthate, 5-bromo-3-isopropyl-6-methyluracil, 3-cyclohexyl-6-methyluracil, 3-cyclohexyl-6-sec.butyluracil, 3-cyclohexyl-5-bromouracil, 3-cyclohexyl-5-chlorouracil, 3-cyclohexyl-5,6-trimethylene uracil, 3-isopropyl-5-chlorouracil, 3-isopropyl-5-bromouracil, 2-chloro-N-ethyl-4-thiocyanato-aniline, 2,3,6-trichlorobenzyloxypropanol hexachloro-2-propanone, sodium 2-(2,4,5-trichlorophenoxy)-ethylsulphate, potassium cyanate, 3,5-dibromo-4hydroxybenzaldoxime-2',4'-dinitrophenyl ether, 3,5-diiodo-4-hydroxybenzaldoxime-2',4'-dinitrophenyl ether, acrolein arsenates allyl alcohol 2,4-dinitrophenyl-2,4-dinitro-6-sec.butylphenyl carbonate, 5-chloro-2-isopropylbenzimidazole 5-iodo-2-trifluoromethyl-benzimidazole, 3-cyclohexyl-6,7-dihydro-1H-cyclopentapyrimidine-2,4-(3H,5H)dione, 1:1-ethylene-2:2-bipyridylium bromide, 1,1-dimethyl-4,4'-bipyridylium dimethylsulphate, di(methoxythiocarbonyl)disulphide, 2-methyl-4-(3'-trifluoromethylphenyl)-tetrahydro-1,2,4-oxadiazine-3,5-dione, 1-phenyl-4,5-dimethoxy-6-pyridazone, 6-chloro-2-difluoromethyl-3H-imidazo(4,5-b)pyridine, 2-tert.butyl-6-chloroimidazo-4,5-pyridine, 5-amino-4-bromo-2-phenylpyridazin-3-one, hexafluoroacetone hydrate, 3,5-dinitro-4-dipropylamino benzenesulphonamide cacodyl, 4-(methylsulphonyl)-2,6-dinitro-N,N-dipropylaniline, 4-methyl-2,6-dinitro,-N,N-dipropylaniline, 5-amino-4-chloro-2-phenyl-3-pyridazone, 2,3,5-trichloro-4-pyridinol, 3,4,5,6-tetrahydro-3,5-dimethyl-1,3,5-thiadiazine-2-thione, sodium 2-(2,4-dichlorophenoxy)ethylsulphate, 2,3-dichloro-1,4-napthoquinone, di(ethoxythiocarbonyl)-disulphide, 3,5-dichloro-2,6-difluoro-4-hydroxypyridine.

Such compositions may be in the form of solutions, emulsions, suspensions, spraying powders, granulates or dusting powders. Other pesticidal substances may, however, also be added. The methods of application depend on the end uses and must ensure a fine distribution of the active substance. Especially for the total destruction of plants, in premature drying out and in defoliating, the activity can be reinforced by the use of basically phytotoxic carriers, for example, high-boiling mineral oil fractions or chlorinated hydrocarbons; on the other hand, the selectivity of the growth inhibition is in general of distinct importance when carriers are used that are inert towards the plants, for example in selective weed control.

For the manufacture of solutions there may be used solvents, especially alcohols, for example, ethanol or isopropanol; ketones, for example, acetone or cyclohexanone; aliphatic hydrocarbons, such as kerosene or cyclic hydrocarbons for example, benzene, toluene, xylene, cyclohexane, tetrahydronaphthalene, alkylated napthalene; also, chlorinated hydrocarbons, for example tetrachloroethane, ethylene chloride; and finally too, mineral and vegetable oils or mixtures of the above-mentioned substances.

The aqueous compositions are preferably emulsions or suspensions. The active substances are homogenized in water as such or in one of the above-mentioned solvents, preferably with the aid of wetting or dispersing agents. Suitable cationic emulsifying or suspending agents are, for example, quaternary ammonium compounds; anionic ones are, for example, soaps, aliphatic long-chained sulphuric acid monoesters, aliphatic-aromatic sulphonic acids, long-chained alkoxyacetic acids; nonionic ones are, for example, polyglycolethers of fatty alcohols or ethylene oxide condensation products with p-tert.alkylphenols. On the other hand, it is also possible to manufacture concentrates consisting of active substance, dispersant and, if desired, solvent. Such concentrates can be diluted before use, for example, with water.

Dusting compositions may be manufactured by mixing or conjoint grinding of the active substance with a solid carrier. Such solid carriers are, for example, talcum, diatomaceous earth, kaolin, bentonite, calcium carbonate, boric acid, tricalcium phosphate, wood meal, cork meal, coal and other materials of vegetable origin. Alternatively, the substances may be absorbed onto the carrier with a volatile solvent. By addition of wetting agents and protective colloids, pulverulent compositions and pastes may be suspendible in water and used as sprays.

In many cases it is advantageous to apply granulates to ensure a uniform release of active substances over a prolonged period of time. These granulates can be prepared by dissolving the active substance in an organic solvent, absorbing this solution by a granulated mineral, for example, attapulgite or $SiO_2$, and removing the solvent.

Polymer granulates may also be used. These granulates can be prepared in such a way that the active substances of formula I are mixed with polymerizable compounds (urea/formaldehyde, dicyandiamide/formaldehyde, melamine/formaldehyde or others), whereupon a mild polymerization is carried out that does not affect the active substances, and with the granulation being effected during the gel formation. It is of greater advantage to impregnate finished, porous polymer granulates (urea/formaldehyde, polyacrylonitrile, polyester or others) that have a specific surface and a favourable adsorption/desorption ratio that can be predetermined, with the active substances, for example in the form of their solutions (in a low boiling solvent) and to remove the solvent.

Polymer granulates of this kind can also be manufactured in the form of microgranulates having bulk weights of preferably 300 g/liter to 600 g/liter and may be distributed with the aid of atomizers. The dusting may be carried out from aircraft over extensive grain cultures.

Additional pesticides, fertilizers, surface-active agents, or substances for increasing the specific weight (for example $BaSO_4$) may, of course, be added to the granulates.

It is also possible to obtain granulates by rendering the carrier compact with the active substances and additives and then comminuting it.

The content of active substance in the compositions described above varies from 0.1 to 95%; and in this respect it should be mentioned that when the composition is applied from an aircraft or by other suitable means of application, concentrations of up to 99.5% or even commercial pure active substance may be used.

The new thiolcarbamates of formula I can be manufactured in simple manner, for example by causing a benzylmercaptan of the formula 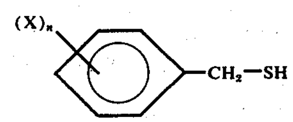 (II)

wherein the symbols X and *n* have the meanings as indicated initially, or a corresponding alkali metal salt, to react with a carbaminic acid halide of the formula 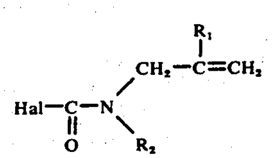 (III)

wherein $R_1$ and $R_2$ have the meaning as indicated and "Hal" represents a chlorine or a bromine atom.

The compounds of formula I can also be obtained by the reaction of a chlorocarbonic acid thioester of the formula 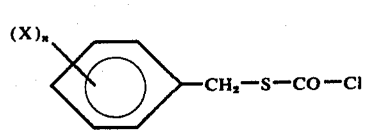 with an amine of the formula 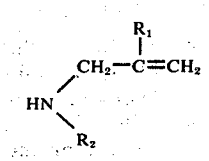 In a further variant process, compounds of formula I can be obtained by the reaction of carbon oxysulphide COS with the amine of the formula 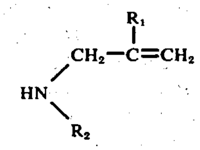 and further reaction with a benzyl compound of the formula 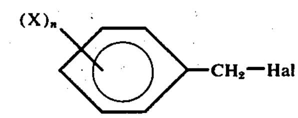 The generally maintained substituents in the structural formulae have the meaning as indicated for formula I and formula III respectively.

The above-mentioned methods for the manufacture of the new thiolcarbamates are known.

EXAMPLE 1

A. Manufacture of N-allyl-N-methyl-S-(p-chlorobenzyl)-thiolcarbamate (Compound No. 1)

49 g of p-chlorobenzylmercaptan was added dropwise to a solution of the Na-methylate from 6.9 g of Na-metal (0.3 mols) in 150 ml of methanol. While cooling to a temperature of 5°–10° C, 40 g of N-allyl-N-methyl-carbamoylchloride (0.3 mols) was dropped into the solution of the mercaptide (in the course of which NaCl was deposited). The batch was stirred for 2 hours at room temperature and for 30 minutes at 40° C. After it had cooled, it was diluted with water, and the oily layer was separated and dissolved in benzene. The organic phase was dried over $Na_2SO_4$ and the solvent removed in vacuo. 65 g of the compound remained as a yellow oil (90% of theory), boiling point 138°–140° C at 0.02 mm Hg.

B. Manufacture of N-n-propyl-N-methallyl-S-(p-chlorobenzyl)-thiolcarbamate (Compound No. 2)

Approx. 35 g of COS (0.58 mols) is injected at a temperature from 0° to 5° C into a solution from 56.5 g of n-propylmethallylamine (0.5 mols), 50.5 g of triethylamine (0.5 mols) and 200 ml of absolute toluene. The solution is left to stand overnight at this temperature. Then 70 g of 4-chlorobenzylchloride (0.435 mols) is added dropwise over the course of 1 hour at room temperature and the batch stirred for a further 1 hour at 50° C. Approx. 500 ml of water is then added, the organic phase is separated, washed with water and dried with $Na_2SO_4$. After the solvent has been removed in vacuo, 130 g (100% of theory) of final product remains as a yellow oil, $n_D^{20}$ 1.5538.

| Analysis for $C_{15}H_{20}$ Cl NOS: | | |
|---|---|---|
| | calculated | found |
| For Cl | 11.90% | 12.3% |

The following compounds may be manufactured in an analogous manner:

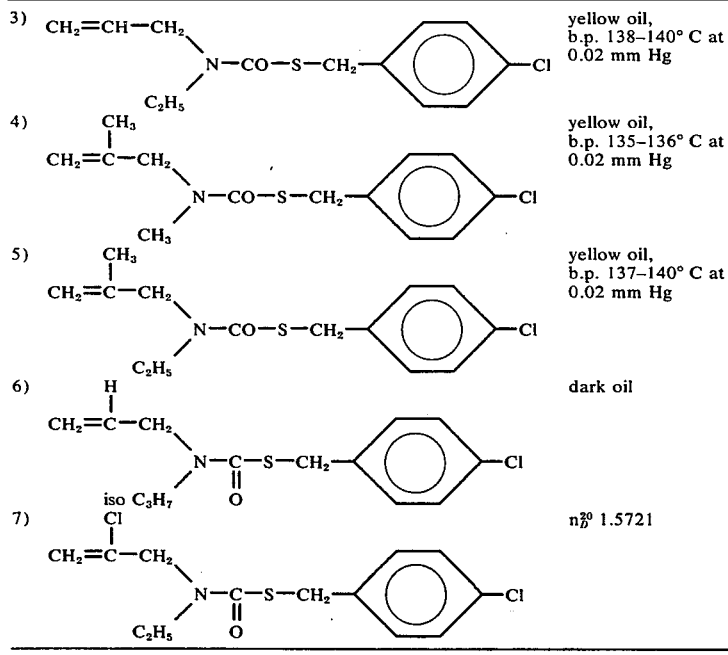

| | | |
|---|---|---|
| 3) | | yellow oil, b.p. 138–140° C at 0.02 mm Hg |
| 4) | | yellow oil, b.p. 135–136° C at 0.02 mm Hg |
| 5) | | yellow oil, b.p. 137–140° C at 0.02 mm Hg |
| 6) | | dark oil |
| 7) | | $n_D^{20}$ 1.5721 |

EXAMPLE 2

40 parts of one of the active substances Nos. 1 to 7 is mixed with 10 parts of a mixture from an anionic surface-active compound, preferably of the calcium or magnesium salt of monolaurylbenzene-monosulphonic acid, and a nonionic surface-active compound, preferably a polyethylene glycol ether of mono-sorbitol-laurate, and the whole dissolved in a small amount of xylene. The mixture is made up to 100 ml of xylene.

A clear solution is thus obtained which may be used as a liquid spray concentrate and can be emulsified by pouring into water.

EXAMPLE 3

8 g of an active substance of Example 1 is dissolved in 20 ml of a 25% strength xylene solution of the emulsifiers Toximul MP and Toximul S (present in the ratio of 1:1). A 40% strength emulsion concentrate is thus obtained that can be diluted with water to any desired extent to give stable emulsions.

EXAMPLE 4

7.5 g of one of the active substances Nos. 1 to 7 is dissolved in 100 ml of acetone and the acetone solution thus obtained is added to 92 g of granulated attapulgite (mesh size: 24/28=meshes/inch). The whole is well mixed and the solvent then removed in a rotational evaporator. A granular material containing 7.5% of active substance is thus obtained. This granular material is particularly well suited to combating Panicum in water rice.

EXAMPLE 5

A. Comparative Test of active Substances in Rice Cultures in the Pre-emergence Treatment Echinochloa crusgalli and rice of the Caloro variety are sown in the 1 cm deep topmost soil layer of earth filled asbestos cement dishes measuring 60 × 60 cm. The surface of the earth is covered with 0.5 cm of water, into which granulates containing 7.5% of an active substance are introduced. The rates of application correspond to 1 kg of active substance per hectare and 2 kg of active substance per hectare. As soon as the plants have emerged after 5 days, the water level is raised to such a height (approx. 2 cms) that the tips of the plants protrude above it.

The evaluation is carried out 40 days after the application. Compounds Nos. 1 and 3 achieved the following result compared with the compound A [N,N-diethyl-S-(p-chlorobenzyl)-thiolcarbamate]:

| Comp. No. | Rate of Application kg a.i./ha | Rice (Caloro) | Echinochloa |
|---|---|---|---|
| 1 | 1 | 1 | 9 |
| | 2 | 1 | 9 |
| 3 | 1 | 1 | 9 |
| | 2 | 1 | 9 |
| A | 1 | 7 | 9 |
| | 2 | 9 | 9 |

Ratings: 1–2 = no damage, 3–4 = temporary damage, 5–7 = severe damage, 8–9 = plants no longer show signs of life.

B. Comparative Test of active Substances in Rice Cultures in the Post-emergence Treatment Rice and Echinochloa seed are sown in the topmost layer of soil in earth filled asbestos cement dishes measuring 60 × 60 cm. After 8 days, when the Echinochloa plants are in the two leaf stage, the well moistened soil is covered with water to a height of 2 cms. Granulates containing 7.5% of an active substance are introduced into the water, ensuring a rate of application of 1, 2 and 4 kg of active substance per hectare.

Evaluation takes place 25 days after the treatment with the granulates.

Compounds Nos. 1 and 3 according to the invention with compound A as comparative substance achieved the following selective action:

| Rate of Application kg a.i./ha | A | | No.1 | | No.3 | |
| --- | --- | --- | --- | --- | --- | --- |
| | Rice | Ech. | Rice | Ech. | Rice | Ech. |
| 1 | 1 | 9 | 1 | 9 | 1 | 9 |
| 2 | 1 | 9 | 1 | 9 | 1 | 9 |
| 4 | 1 | 9 | 1 | 9 | 1 | 9 |

The rating corresponds to test A.

C. Combating of Echinochloa in Planted Water Rice (Post-emergence Treatment)

25 days old rice plants are planted in earth filled asbestos cement dishes measuring 60 × 60 cm. Echinochloa seeds are sown in the 2 cms deep topmost layer of soil. After 12 days, when the emerged plants are in the three leaf stage, the well moistened soil is covered to a height of 2.5 cms with a layer of water, into which granulates containing 7.5% of an active substance are introduced, representing a rate of application of 2, 4 and 6 kg of active substance per hectare.

The evaluation takes place 12 and 25 days after the treatment with the granulates.

The compounds Nos. 1 and 3 according to the invention and the comparative substances A achieved the following selective action:

| Rate of Application kg a.i./ha | After 12 days | | | | | |
| --- | --- | --- | --- | --- | --- | --- |
| | A | | No. 1 | | No. 3 | |
| | Rice | Ech. | Rice | Ech. | Rice | Ech. |
| 2 | 1 | 3 | 1 | 6 | 1 | 5 |
| 4 | 1 | 6 | 1 | 7 | 1 | 6 |
| 6 | 1 | 7 | 1 | 7 | 1 | 7 |

| Rate of Application kg a.i./ha | After 25 days | | | | | |
| --- | --- | --- | --- | --- | --- | --- |
| | A | | No. 1 | | No. 3 | |
| | Rice | Ech. | Rice | Ech. | Rice | Ech. |
| 2 | 1 | 9 | 1 | 9 | 1 | 9 |
| 4 | 1 | 9 | 1 | 9 | 1 | 9 |
| 6 | 1 | 9 | 1 | 9 | 1 | 9 |

The rating corresponds to test A.

Result: In the low application rate of 2 kg of active substance per hectare, the compounds Nos. 1 and 3 according to the invention possess a markedly more rapid selective action than compound A.

I claim:

1. A method for combatting undesired grasses in rice cultures which comprises applying thereto a herbicidally effective amount of N-methyl-N-allyl-S-p-chlorobenzyl-thiolcarbamate.

2. A method for combatting undesired grasses in rice cultures which comprises applying thereto a herbicidally effective amount of N-ethyl-N-allyl-S-p-chlorobenzyl-thiolcarbamate.

3. A method for combatting undesired grasses in rice cultures which comprises applying thereto, after emergence of the grasses and after planting or emergence of the rice, a herbicidally effective amount of N-methyl-N-methallyl-S-p-chlorobenzyl-thiolcarbamate.

* * * * *